| United States Patent [19] | [11] | 4,053,380 |
|---|---|---|
| Fujita et al. | [45] | Oct. 11, 1977 |

[54] 1,1,1-TRIHALOGENO-4-METHYLPENTENES, METHOD OF PREPARING THE SAME AND USE OF THE SAME IN THE PREPARATION OF 1,1-DIHALOGENO-4-METHYL-1,3-PENTADIENES

[75] Inventors: Yoshiji Fujita, Kurashiki; Yoshiaki Omura, Mitsu; Fumio Mori, Kurashiki; Kazuo Itoi, Kurashiki; Takashi Nishida, Kurashiki; Yoshin Tamai, Kurashiki; Sukeji Aihara, Kurashiki; Takeo Hosogai, Kurashiki; Fumio Wada, Kurashiki, all of Japan

[73] Assignee: Kurraray Co., Ltd., Kurashiki, Japan

[21] Appl. No.: 676,517

[22] Filed: Apr. 13, 1976

[30] Foreign Application Priority Data

| Apr. 14, 1975 | Japan | 50-45068 |
| May 12, 1975 | Japan | 50-57124 |
| June 16, 1975 | Japan | 50-72923 |
| June 25, 1975 | Japan | 50-79561 |
| June 27, 1975 | Japan | 50-79802 |

[51] Int. Cl.$^2$ .......................... B01J 1/10; C07C 21/02
[52] U.S. Cl. .......................... 204/163 R; 260/654 R; 260/654 D; 260/655
[58] Field of Search ............... 204/163 R; 260/654 R, 260/654 D, 655

[56] References Cited

PUBLICATIONS

Farkas et al., Chem. Abs., vol. 52, pp. 13650 to 13651 (1958).
Cazaux et al., Chem. Abs., vol. 72, 11784w, p. 245 (1970).
Farkas et al., Collection Czechoslov. Chem. Commun., vol. 24 (1959) pp. 2230 to 2236.

*Primary Examiner*—Leland A. Sebastian
*Attorney, Agent, or Firm*—Bacon & Thomas

[57] ABSTRACT

1,1,1-Trihalogeno-4-methyl pentenes and 1,1-dihalogeno-4-methyl-1,3-pentadienes are produced. These compounds are of value as intermediates for the production of pyrethrin analogs which are of use as insecticides or agricultural chemicals.

41 Claims, No Drawings

1,1,1-TRIHALOGENO-4-METHYLPENTENES, METHOD OF PREPARING THE SAME AND USE OF THE SAME IN THE PREPARATION OF 1,1-DIHALOGENO-4-METHYL-1,3-PENTADIENES

The present invention relates to 1,1,1-trihalogeno-4-methylpentenes, a method for producing the same, and a method for producing 1,1-dihalogeno-4-methyl-1,3-pentadienes from 1,1,1-trihalogeno-4-methylpentenes.

1,1,1-Trihalogeno-4-methylpentenes according to the present invention are novel compounds having the general formula:

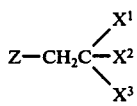

[I]

(wherein $X^1$, $X^2$ and $X^3$ are the same or different and each represents a halogen atom; Z stands for a group of the formula:

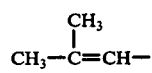

or a group of the formula:

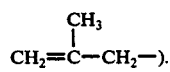

Referring to general formula [I], $X^1$, $X^2$ and $X^3$, respectively, stand for a chlorine, bromine, fluorine or iodine atom, the preferred species being chlorine and bromine. The 1,1,1-trihalogeno-4-methylpentenes represented by general formula [I] are of value as starting materials for the production of various important compounds.

Among the compounds of general formula [I], 1,1,1-trihalogeno-4-methyl-3-pentenes in particular are important intermediates for the synthesis of dihalogeno-vinyl chrysanthemumates which, as will be explained hereinafter, have recently come to claim attention as insecticides or agricultural chemicals and are of value also as intermediates for the synthesis of terpenoids. Furthermore, 1,1,1-trihalogeno-4-methyl-4-pentenes, after isomeric conversion to 1,1,1-trihalogeno-4-methyl-3-pentenes, are similarly of use as intermediates for the synthesis of dihalogeno-vinyl chrysanthemumates and other compounds. Dihalogeno-vinyl chrysanthemumates have high and sustained insecticidal activity against various species of insects in contrast to natural pyrethroid insecticides which are susceptible to photolysis [M. Elliot et al, Nature 244, 456 (1973)].

As a process for the synthesis of dihalogeno-vinyl chrysanthemumates, Japanese Patent Application Laid Open No. 47531/1974 (corresponding to Ger. Pat. Appl. Laid Open No. 2326077) recently teaches a process which comprises oxidizing chrysanthemum-monocarboxylic acid with ozone and subjecting the resultant correspnding aldehyde to the Wittig reaction. This process, however, is generally thought to be hardly adaptable to commercial production because it requires not only a costly starting material, i.e. chrysanthemummonocarboxylic acid but such time-consuming reactions as oxidation with ozone and Wittig reaction.

Also recently disclosed is a process which comprises permitting an orthocarboxylic acid ester to act upon 3-methyl-2-buten-1-ol, then adding a tetrahalogenomethane to the reaction product and cyclizing the resultant adduct with alkali to obtain a cyclopropanecarboxylate. Since this process requires only a few reaction steps, each providing a good yield, it might appear to be commercially profitable. However, this process also has much to be desired partly because, up to this time, no effective synthetic route to the starting material 3-methyl-2-buten-1-1-ol is known and partly because of the high prices of orthocarboxylic acid esters.

J. Farkas et al report a diazoacetic acid process in Collect. Czech. Chem. Commun. 24, 2230 (1959) (hereinafter referred to as Farkas process). This process comprises acetylating 1,1,1-trichloro-4-methyl-3-penten-2-ol, reducing the acetylation product with zinc-acetic acid to obtain 1,1-dichloro-4-methyl-1,3-pentadiene and, then in a conventional manner, reacting the last-mentioned compound with diazoacetic acid or an ester thereof to obtain a cyclopropanecarboxylic acid or an ester thereof. This process is not commercially profitable, either, for it involves a time-consuming series of reactions for the synthesis of 1,1-dichloro-4-methyl-1,3-pentadiene and, also, a complicated procedure, i.e. reduction with zinc-acetic acid.

The research undertaken by us to develop a method for economical production of dihalogeno-vinyl chrysanthemumates led to the discovery of a synthetic intermediate which is instrumental in realizing a marked improvement in the Farkas process.

Thus, 1,1,1-trihalogeno-4-methyl-3-pentenes are considerably superior to conventional 1,1,1-trihalogeno-2-acetoxy-4-methyl-3-pentenes as intermediate materials for the production of 1,1-dihalogeno-4-methyl-1,3-pentadienes according to the Farkas process. When a 1,1,1-trihalogeno-4-methyl-3-pentene is employed, this material can be easily converted to the 1,1-dihalogeno-4-methyl-1,3-pentadiene of general formula [II] by a simple procedure, i.e. treatment with a basic reagent, as compared to the conventional costly and complicated procedure, i.e. using a stoichiometric amount of zinc for the reduction of a 1,1,1-trihalogeno-2-acetoxy-4-methyl-3-pentene with zinc-acetic acid.

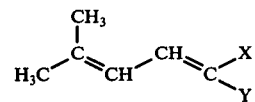

[II]

(wherein X and Y, respectively, represent one of $X^1$, $X^2$ and $X^3$ of general formula [I])

As examples of said basic reagent, there may be mentioned alkali metal or alkaline earth metal hydroxides such as sodium hydroxide, potassium hydroxide, calcium hydroxide, barium hydroxide, etc.; alkali metal alcoholates such as sodium methoxide, sodium ethoxide, potassium methoxide, sodium tert-butoxide, potassium tert-butoxide, sodium tert-amyloxide, etc.; alkali metal hydrides such as sodium hydride, potassium hydride, etc.; alkali metal amindes such as sodium amide, etc.; organic amines such as 1,5-diazabicyclo[3,4,0]nonene-5 (briefly DBN), 1,5-diazabicyclo[5,4,0]undecene-5(briefly OBU), 2-dimethylamino-1-pyrroline, etc.; and organolithium compounds such as n-butyllithium, s-butyllithium, diisopropylaminolithium, and so forth. From the standpoints of economy and reaction efficiency, it is preferable to employ alkali metal alcoholates, alkali metal hydrides or alkali metal hydroxides. The proportion of said basic reagent is at least one molecular equivalent and, preferably, within the range of 1 to 2 equivalents.

The reaction is preferably carried out in a solvent. As examples of said solvent, there may be mentioned aqueous solvents; alcohol solvents such as methanol, ethanol, etc.; aprotonic polar solvents such as N,N-dimethylformamide (hereinafter DMF), dimethylsulfoxide (briefly DMSO), etc.; and hydrocarbons such as benzene, toluene and so forth. When the basic reagent is an organic amine, it may be used in excess so that it will act also as a solvent. The reaction temperature is between room temperature and 150° C, preferably within the range of 50° to 130° C.

As illustrated hereinafter, a 1,1,1-trihalogeno-4-methyl-3-pentene may be reacted with diazoacetic acid or an ester thereof in a manner conventional per se and, then, the reaction product be de-hydrohalogenated to obtain the corresponding dihalogeno-vinyl chrysanthemumic acid or an ester thereof.

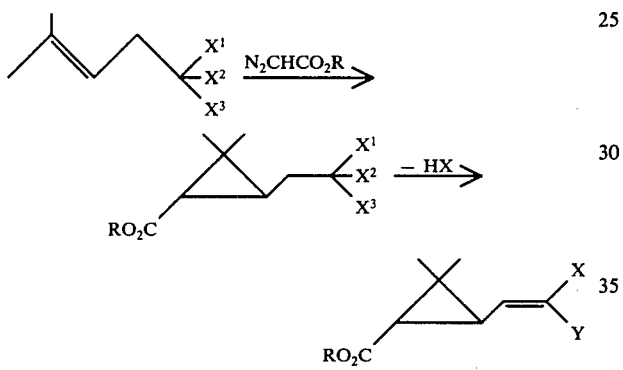

(wherein X and Y, respectively, represent one of $X^1$, $X^2$ and $X^3$; and R is a hydrogen atom or an alcohol residue)

The 1,1,1-trihalogeno-4-methylpentenes [I] of the present invention may be produced by removing R'OH from compounds of general formula [III]:

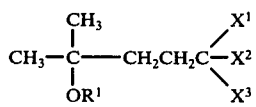

[III]

(wherein $R^1$ is a hydrogen atom or an alkyl, cycloalkyl, aryl, aralkyl or acyl group; $X^1$, $X^2$ and $X^3$ have the same meanings as defined in general formula [I]).

More particularly, compounds of general formula [III] are such that $R^1$ is a hydrogen atom, an alkyl group of 1 to 20 carbon atoms, a cycloalkyl group of 6 to 20 carbon atoms, an aryl group of 6 to 15 carbon atoms, an aralkyl group of 7 to 20 carbon atoms or an acyl group of 1 to 10 carbon atoms, preferably representing hydrogen, methyl, ethyl, propyl, butyl, acetyl, propionyl, or butyryl, and $X^1$, $X^2$ and $X^3$, respectively, are preferably chlorine or bromine.

The reaction by which $R^1OH$ is removed from a compound of general formula [III] is (i) dehydration where $R^1$ is a hydrogen atom, (ii) dealcoholation where $R^1$ is an alkyl, cycloalkyl, aryl or aralkyl group, and (iii) decarboxylation where $R^1$ is an acyl group.

The above dehydration, dealcoholation or decarboxylation reaction may be easily accomplished by heating a compound of general formula [III] in the presence of a strongly acid to weakly acid catalyst such as sulfuric acid, phosphoric acid, p-toluenesulfonic acid, phosphorus pentoxide, vanadium pentoxide, wolfram trioxide, etc. at a temperature ranging from room temperature to 120° C or, alternatively, heating the same either in gaseous phase or in liquid phase in the presence of silica gel, aluminum silicate, kieselguhr, pumice, Fuller's earth, activated alumina, activated carbon or the like at a temperature from 80° to 250° C. In the latter case, Kieselguhr, for instance, may be used in combination with vanadium pentoxide, for instance, in the form of a supported catalyst to hasten the reaction.

The aforementioned catalysts is used in a proportion of 0.01 to 30 weight percent, preferably 0.1 to 10 weight percent, based on compound of general formula [III].

While the composition of the reaction product varies somewhat according to the conditions of reaction, the dehydration, dealcoholation or decarboxylation of compounds of general formula [III] yields, as principal product compounds, 1,1,1-trihalogeno-4-methyl-3-pentene of general formula [I']:

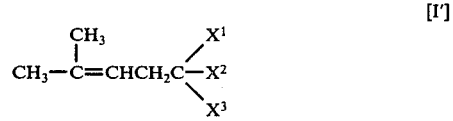

[I']

and 1,1,1-trihalogeno-4-methyl-4-pentene of general formula [I'']:

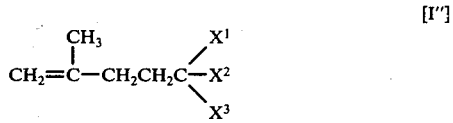

[I'']

In addition, byproducts such as 1,1-dihalogeno-4-methyl-1,3-pentadiene, etc. are also produced in minor amounts.

Normally, the total selectivity for compound [I'] and compound [I''] is not less than 98 percent at a conversion of not less than 95 percent based on compound of general formula [III]. The ratio of 1,1,1-trihalogeno-4-methyl-3-pentene to 1,1,1-trihalogeno-4-methyl-4-pentene in the reaction product is normally within the range of 3 : 2 to 9 : 1, and by fractional distillation, 1,1,1-trihalogeno-4-methyl-3-pentene can be isolated in high purity. In connection with this procedure, it is of utmost significance, for the purpose of producing a starting material for 1,1-dihalogeno-4-methyl-1,3-pentadiene, to isomerize the 1,1,1-trihalogeno-4-methyl-4-pentene, which is obtainable as a first distillate in the above procedure, to the correspnding 1,1,1-trihalogeno-4-methyl-3-pentene.

If this first distillate rich in 1,1,1-trihalogeno-4-methyl-4-pentene is returned to the reaction system of compound [III] in the presence of the aforementioned acid catalyst, it will isomerize to 1,1,1-trihalogeno-4-methyl-3-pentene. In this manner, 1,1,1-trihalogeno-4-methyl-3-pentene can be produced in good yield.

The isomerization of 1,1,1-trihalogeno-4-methyl-4-pentene to 1,1,1-trihalogeno-4-methyl-3-pentene may also be accomplished in an independent reaction step. In such a process, the reaction may be conducted between about 80° C and about 200° C. particularly preferred is a temperature range of about 110° to 170° C. This isomerization reaction proceeds with heating time until finally it yields an equilibrium composition corresponding to the temperature employed.

While said isomerization reaction proceeds under heating even in the absence of a catalyst, the following procedure may be followed to obtain a significantly increased rate of isomerization and to drastically reduce the reaction time required before an equilibrium composition or a conversion rate approaching it is obtained. Thus, the reaction system may be heated in the presence of, as a catalyst, at least a member selected from the class consisting of transition metals of Group 6B, Group 7B and Group 8 of Periodic Table of the Elements (such as Cr, Mn, Co, Ni, Ru, Ph, Pd, W, Ir, etc.) and compounds (e.g. oxides, inorganic acid salts, organic acid salts, complex compounds, etc.) of such transition metals. As an alternative, the reaction system may be heated in the presence of an acid catalyst such as sulfuric acid, phosphoric acid, boric acid, p-toluenesulfonic acid, acetonedisulfonic acid or the like.

Referring to the catalysts thus employable, the compounds of transition metals of Group 6B, Group 7B and Group 8 are exemplified by chromium (III) acetylacetonate, molybdenum disulfide, wolfram trioxide, manganese (III) acetylacetonate, ruthenium trichloride, cobalt (II) acetylacetonate, cobalt hexamine chloride, rhodium (III) acetylacetonate, rhodium trichloride, iridium trichloride, Raney nickel, nickel (II) acetylacetonnate, palladium chloride, palladium black, palladium oxide, palladium acetate, 5% palladium-on-carbon and so forth. The catalyst may be employed in an amount ranging from 0.001 to 30 weight percent based on compound [I″] and, preferably, 0.1 to 10 weight percent on the same basis. The isomerization reaction may be carried out either batchwise or continuously.

A compound [III] may be produced by adding a haloform to dimethyl vinyl carbinol or a derivative thereof, of general formula [IV], under conditions of radical reaction.

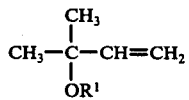

[IV]

(wherein $R^1$ is as defined in general formula [III])

The said conditions of radical reaction may be established by allowing a radical initiator to be present in the reaction system or by irradiation. As said radical initiator, there may be mentioned benzoyl peroxide (BPO), azobisisobutyronitrile (AIBN), acetyl peroxide, di-tert-butyl peroxide, tert-butyl hydroperoxide, cumene hydroperoxide and so forth. The radical initiator serves the purpose when used in a catalytic amount. The reaction may be conducted in the atmosphere or, alternatively, in an inert gas such as carbon dioxide, nitrogen, helium or the like.

The haloforms that are preferred for the purposes of this reaction are chloroform and bromoform. It is sufficient to employ a molecular equivalent of haloform based on compound of general formula [IV], although 2 to 20 equivalents of haloform may be employed, in which case the haloform will act also as a reaction solvent. Although a reaction solvent is not indispensable, there may be employed a solvent that will not directly interfere with the contemplated reaction, such solvent being exemplified by carbon disulfide, n-hexane, n-heptane and so forth. The reaction temperature is preferably somewhere between room temperature and 100° C when the reaction is initiated by irradiation, or from 70° to 180° C when a radical reaction initiator is employed.

Radical-addition reactions of halides, esters, alcohols, active methylene, etc. to olefins are well known and, broadly, the following two general procedures are available.

a. Heating in the presence of both of an organic amine and a transition metal compound;
b. Heating in the presence of a radical reaction initiator The first procedure a) is not applicable from a selectivity point of view. Thus, under the conditions of a), the addition of the haloform as X. and .CHX$_2$ radicals predominates. The hitherto attempted radical-addition reaction of a haloform to an allylic alcohol, ether or ester yields a large proportion of telemer, for example as reported by Kharasch et al in J. Am. Chem. Soc. 69, 1105 (1947) and described by Lewis et al in J. Am. Chem. Soc. 76, 457 (1954), and the yield of 1 : 1 abjuct is as low as 20 to 30 percent as stated by Tarrant et al in J. Org. Chem. 26, 4646 (1961). Furthermore, it is known that a tertiary allylic alcohol such as dimethyl vinyl carbinol is ready to induce a dehydration reaction under heating. Notwithstanding this, subjecting a compound of general formula [IV] and a haloform together to the above-mentioned radical-reaction conditions enables one to selectively obtain a compound of general formula [III] without causing a dehydration reaction or being accompanied by telomerization. By way of illustration, we added a small amount of benzoyl peroxide (BPO) to 8.6 g of dimethyl vinyl carbinol in 50 ml of chloroform and reacted the mixture at 140° C and in a nitrogen atmosphere for 16 hours. Gas-chromatographic analysis of the reaction product mixture revealed that the conversion of dimethyl vinyl carbinol was 78.2 percent and the selectivity for 1,1,1-trichloro-4-methyl-4-hexanol was 94.5 percent.

1,1,1-Trihalogeno-4-methyl-3-pentenes may be produced by the following procedure as well, although this procedure is less advantageous than the above procedure starting with compounds of general formula [III] in that the former procedure gives rise to larger amounts of byproducts. Thus, a 1,1,1-trihalogeno-4-methyl-3-pentene may be produced by heating a tertiary allyl halide of general formula [V] together with a tetrahalogenomethane under radical reaction conditions.

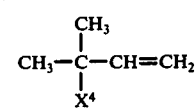

[V]

(wherein $X^4$ is a halogen atom)

The above procedure entails production of a large proportion of a byproduct compound of general formula [VI]:

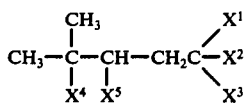

[VI]

(wherein X¹, X² and X³ have the same meanings as defined in general formula [I]; X⁴ has the same meaning as defined in general formula [V]; and X⁵ is a halogen atom)

The present invention will be further illustrated by way of the following examples, in which, unless otherwise specified, all NMR spectra were determined at 60 MHZ in carbon tetrachloride at room temperature, with tetramethylsilane as the internal reference.

EXAMPLE 1

To a solution of 17.2 g of dimethyl vinyl carbinol in 150 ml of chloroform was added 0.8 g of benzoyl peroxide and, in an autoclave, the mixture was reacted at 135° C and in a nitrogen atmosphere for 18 hours. Then, the unreacted dimethyl vinyl carbinol and chloroform were removed by distillation under reduced pressure. As the residue was obtained 30.1 g of a dark-reddish viscous fluid. This residue was subjected to vacuum distillation to obtain 28.2 g (yield 69%) of 1,1,1-trichloro-4-pentanol. Gas-chromatographic analysis of this product showed its purity to be 95.4%. mass spectrometric data suggested that the impurity comprised 1,1,3-trichloro-4-methyl-4-pentanol. The following procedures were used for structural identification of 1,1,1-trichloro-4-methyl-4-pentanol.

Infrared absorption spectrum:

$\begin{cases} 3340, 1380, 1368, 1280, 1220, 1150, 1073, 1035, 942, \\ 910, 795, 745, 695 \text{ cm}^{-1} \end{cases}$ Mass spectrum:

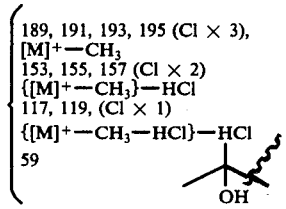

$\begin{cases} 189, 191, 193, 195 \text{ (Cl} \times 3), \\ [M]^+ - CH_3 \\ 153, 155, 157 \text{ (Cl} \times 2) \\ \{[M]^+ - CH_3\} - HCl \\ 117, 119, \text{ (Cl} \times 1) \\ \{[M]^+ - CH_3 - HCl\} - HCl \\ 59 \end{cases}$ Nuclear magnetic resonance spectrum: δ (in CCl₄, ppm)

$\begin{cases} 1.22 \text{ s 6H, CH}_3— \\ \text{ca, } 1.70 - 1.95, \text{ m, 2H, —CH}_2— \\ \text{ca, } 2.64 - 2.92, \text{ m, 2H, —CH}_2— \end{cases}$ Then, 0.1 g of p-toluenesulfonic acid was added to a solution of 10 g of 1,1,1-trichloro-4-methyl-4-pentanol in 50 ml of benzene, and the mixture was heated under reflux for 2 hours, the byproduct water being azeotropically removed. Following the reaction, the solvent was distilled off under reduced pressure and the residue was distilled in vacuo. The procedure provided 8.5 g (yield 92%) of a mixture of 1,1,1-trichloro-4-methyl-4-pentene and 1,1,1-trichloro-4-methyl-3-pentene as a fraction boiling at 74° - 77° (19 mmHg). Gas-chromatographic analysis of this fraction revealed that it comprised 1,1,1-trichloro-4-methyl-4-pentene and 1,1,1-trichloro-4-methyl-3-pentene in a ratio of about 33 to 67. This mixture was fractionated by fractional distillation and each fraction was identified by the following procedures.

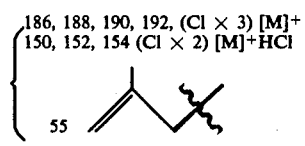

Infrared absorption spectrum (neat)

$\begin{cases} 1650, 1445, 1378, 1255 \\ 1065, 900, 850, 790, 768, 700 \text{ cm}^{-1} \end{cases}$ Mass spectrum $\begin{cases} 186, 188, 190, 192, \text{ (Cl} \times 3) [M]^+ \\ 150, 152, 154 \text{ (Cl} \times 2) [M]^+ + HCl \\ 55 \end{cases}$ Nuclear magnetic resonance spectrum: δ(in CCl₄, ppm)

$\begin{cases} 1.73, \text{ s, 3H, CH}_3— \\ \text{ca, } 2.23 - 2.93, \text{ m, 4H, —CH}_2CH_2— \\ 4.76, \text{ s, 2H, CH}_2=C— \end{cases}$

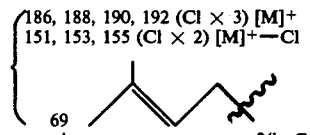

Infrared absorption spectrum (neat)

$\begin{cases} 1670, 1440, 1375, 1105, 1022, 952, \\ 850, 790, 765, 705 \text{ cm}^{-1} \end{cases}$ Mass spectrum $\begin{cases} 186, 188, 190, 192 \text{ (Cl} \times 3) [M]^+ \\ 151, 153, 155 \text{ (Cl} \times 2) [M]^+ - Cl \\ 69 \end{cases}$ Nuclear magnetic resonance spectrum: δ(in CCl₄, ppm)

$\begin{cases} 1.66, 1.75, \text{ each s, 6H, CH}_3—, \\ 3.29, \text{ d, 2H, —CH}_2—, J = 11.5 \text{ Hz} \\ 5.35, \text{ t, 1H, —CH—}, J = 11.5 \text{ Hz} \end{cases}$

EXAMPLES 2 to 8

5.0g of 1,1,1-trichloro-4-methyl-4-pentanol, as obtained by a procedure similar to that described in Example 1, were subjected to dehydration reaction under various conditions. The results are set forth in Table 1. In Examples 2, 6 and 7, the byproduct water was azeotropically removed from the reaction system.

Table 1

| Ex. | Reaction solvent | Dehydrating agent | Conditions of dehydration | % Yield | * 4-Pentene/ 3-pentene |
|---|---|---|---|---|---|
| 2 | C₆H₆ 25 ml | conc H₂SO₄ 50 mg | reflux, 2.0 hr | 91 | 33/67 |
| 3 | Diethyl ether 25 ml | conc H₂SO₄ 1.0 g | reflux, 1.5 hr | 83 | 28/72 |
| 4 | CH₃C₆H₅ 25 ml | P₂O₅ 50 mg | reflux, 3.0 hr | 87 | 36/64 |
| 5 | Diethyl ether 25 ml | P₂O₅ 80 mg | reflux, 6.0 hr | 86 | 30/70 |
| 6 | C₆H₆ 25 ml | V₂O₅ 30 mg | reflux, 8.0 hr | 87 | 35/65 |
| 7 | C₆H₆ 25 ml | WO₃ 20 mg | reflux, 6.0 hr | 89 | 35/65 |
| 8 | (CH₃)₂C₆H₄ 25 ml | SiO₂ 1.0 g | reflux, 4.0 hr | 84 | 40/60 |

* 1,1,1-Trichloro-4-methyl-4-pentene/1,1,1-trichloro-4-methyl-3-pentene

EXAMPLES 9 to 18

As in Example 1, various dimethyl vinyl carbinol compounds were reacted with a haloform under various radical reaction conditions. Following recovery of the excess haloform and unreacted dimethyl vinyl carbinol compound, the residue was not purified but directly subjected to the next reaction for removal of $R^1OH$. The results are summarized in Table 2. In all instances, the radical-addition reaction was conducted in an inert gaseous atmosphere.

EXAMPLE 19

A glass tube, 1.5 cm in inside diameter and 30 cm long, was packed with 2% vanadium pentoxide-on-Kieselguhr and, then, externally heated by ribbon heater to establish an internal temperature of 130° – 135° C. To this tube was fed a solution of 50 g of 1,1,1-trichloro-4-methyl-4-pentanol in 50 ml of toluene at a rate of 30 ml/hr. and the distillate was cooled by condenser and trapped. The distillate was dried over magnesium sulfate and the solvent was distilled off under reduced pressure. Gas-chromatographic analysis of the residue Table 2

| Ex. | $OR^1$ (g) | Haloform (g) | Radical initiator (g) | Conditions of radical addition | Product (OR¹, X¹, X², X³) | %* (Yield) | Conditions of removal of $R_1OH$ | Yield** | ($\Delta^4-/\Delta^3-$) |
|---|---|---|---|---|---|---|---|---|---|
| 9 | $R^1=H$ (8.6) | Chloroform (200) | BPO (0.2) | 170° C, 18 hr | OH, Cl, Cl, Cl | (89.6) | p-Toluenesulfonic acid 0.05 g $C_6H_6$ 25 ml reflux, 1.5 hr | 92.6 | (33/67) |
| 10 | $R^1=H$ (8.6) | Bromoform (50) | t.Butyl peracetate (0.2) | 120° C, 8 hr | OH, Br, Br, Br | (83.3) | $P_2O_5$ 0.2 g $C_6H_6$ 25 ml reflux, 3 hr | 90.3 | (33/65) |
| 11 | $R^1=-C(=O)CH_3$ (12) | Chloroform (100) | BPO (0.4) | 150° C, 12 hr | OCCH₃(=O), Cl, Cl, Cl | (76.2) | conc.$H_2SO_4$ 0.1 g $CH_3C_6H_5$ 25 ml reflux, 2 hr | 94.1 | (35/65) |
| 12 | $R^1=-C(=O)CH_3$ (12) | Chloroform (100) | AIBN (0.3) | 160° C, 12 hr | OCCH₃(=O), Cl, Cl, Cl | (73.8) | P-Toluenesulfonic acid 0.1 g $CCl_4$ 25 ml reflux, 3 hr | 93.8 | (33/67) |
| 13 | $R^1=-C(=O)CH_3$ (12) | Bromoform (50) | BPO (0.2) | 130° C, 8 hr | OCCH₃(=O), Br, Br, Br | (82.6) | conc.$H_2SO_4$ 0.5 g $C_2H_5OC_2H_5$ 50 ml reflux, 5 hr | 91.1 | (30/70) |
| 14 | $R^1=-CH_2C_6H_5$ (15) | Chloroform (200) | t-Butyl perbenzoate (0.3) | 130° C, 18 hr | O-CH₂C₆H₅, Cl, Cl, Cl | (77.4) | conc.$H_2SO_4$ 0.5 g $C_2H_5OC_2H_5$ 50 ml reflux, 6 hr | 86.7 | (28/72) |
| 15 | $R^1=-CH_3$ (10) | Chloroform (200) | Cumene hydroperoxide (0.5) | 140° C, 16 hr | OCH₃, Cl, Cl, Cl | (69.6) | Conc.$H_2SO_4$ 0.1 g No solvent 90° C, 8 hr | 85.5 | (32/68) |
| 16 | $R^1=-C_2H_5$ (12) | Chloroform (200) | Cumene Hydroperoxide (0.5) | 130° C, 14 hr | OC₂H₅, Cl, Cl, Cl | (65.2) | Conc.$H_2SO_4$ 0.1 g No solvent 90° C, 8 hr | 87.0 | (33/67) |
| 17 | $R^1=-C_2H_5$ (12) | Bromoform (50) | t-Butyl hydroperoxide (0.2) | 120° C, 14 hr | OC₂H₅, Br, Br, Br | (74.5) | $V_2O_5$ 0.2 g $C_6H_6$ 25 ml reflux, 3 hr | 86.2 | (31/69) |
| 18 | $R^1=$ cyclohexyl (15) | Chloroform (200) | BPO (0.4) | 130° C, 20 hr | O-C₆H₁₁, Cl, Cl, Cl | (70.2) | conc. $H_2SO_4$ 0.3 g $C_6H_6$ 25 ml reflux, 6 hr | 80.4 | (32/68) |

*Each yield value was determined by gas-chromatographic analysis of the concentration residue.
**Each yield value represents the yield of distillative isolation. The $\Delta^4-/\Delta^3-$ values in parentheses denote the ratios of 1,1,1-trihalogeno-4-methyl-4-pentene to 1,1,1-trihalogeno-4-methyl-3-pentene.

revealed that the conversion of 1,1,1-trichloro-4-methyl-4-pentanol was 93.6%, the selectively for the contemplated 1,1,1-trichloro-4-methyl-4-pentene and 1,1,1-trichloro-4-methyl-3-pentene was 98.7% and the ratio of the 4-pentene to the 3-pentene was 43 : 57.

EXAMPLE 20

A three-necked flask of 200 ml capacity was filled with 68 g of isoprene and, at 0° - 3° C, 1.0 mole of dry hydrogen chlorine gas was introduced. Following the reaction, the system was further stirred at the same temperature for an hour and, then, distilled under reduced pressure. From the fraction boiling at 46° - 47° C (214 mmHg) was obtained 79.0 g (yield 76%) of 1,2-prenyl chloride. A 20.8 g portion of this 1,2-prenyl chloride was dissolved in 79 g of bromotrichloromethane, followed by the addition of 1.2 g of benzoyl peroxide. The reaction was thus carried out at 80° ± 2° C for 16 hours. The reaction mixture was directly distilled under reduced pressure to obtain 9.7 of 1,1,1-trichloro-4-methyl-3-pentene (26% from 1,2-prenyl chloride) as a fraction boiling at 77° -78° C (20 mmHg) and 37.2 g of 1,1,1,4-tetrachloro-3-bromo-4-methylpentane (62% from 1,2-prenyl chloride) as a fraction boiling at 89° - 91° C (1.2 mmHg).

By the procedure described in Example 1, the above 1,1,1-trichloro-4-methyl-3-pentene was structurally identified with the 1,1,1-trichloro-4-methyl-3-pentene obtained in Example 1. The structural identification for 1,1,1,4-tetrachloro-3-bromo-4-methylpentane was carried out by the following procedures.

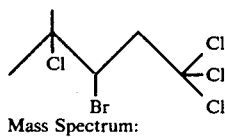
Mass Spectrum:

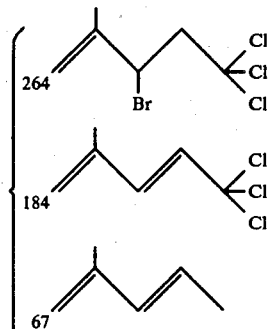

Nuclear magnetic resonsance spectrum: δ (in CCl$_4$, ppm)

{ 1.82, 1.98: each s, 6H, CH$_3$—
3.15: dd, 2H, —CH$_2$—
4.35: dd, 1H, —CH—
                |
                Br }

EXAMPLES 21 to 27

Various tertiary allyl halides were each subjected to radical reaction with bromotrichloromethane or carbon tetrachloride under various conditions. The results are set forth in Table 3. All reactions were conducted in an inert gaseous atmosphere.

Table 3

| Ex. | ![CH3/CH3/X4 structure] | (g) | Z—C(X¹)(X²)(X³) | (g) | Radical initiator (g) | Conditions of reaction | R¹—/X¹/X²/X³ structure | (%) | R¹/R²/X⁴/Z/X¹/X²/X³ structure | (%) |
|---|---|---|---|---|---|---|---|---|---|---|
| 21 | (X⁴=Cl) | (10.4) | BrCCl₃ | (50) | t-Butyl perbenzoate (0.5) | 105° C, 13 hr | Cl,Cl,Cl product | (43) | Cl,Br,Cl,Cl product | (32) |
| 22 | " | (") | " | (") | di-t-Butyl peroxide (0.6) | 80° C, 16 hr | " | (14) | " | (67) |
| 23 | " | (") | " | (") | BPO (0.5) | 90° C, 24 hr | " | (18) | " | (64) |
| 24 | " | (") | " | (") | Methyl ethyl ketone peroxide (0.4) | 80° C, 32 hr | " | (11) | " | (45) |
| 25 | " | (") | CHCl₃ | (300) | di-t-Butyl peroxide (0.5) | 100° C, 48 hr | " | (24) | Cl,Cl,Cl* product | (33) |
| 26 | " | (") | CCl₄ | (200) | t-Butyl perbenzoate (0.5) | 100° C, 40 hr | " | (25) | Cl,Cl**,Cl,Cl product | (38) |
| 27 | " | (") | CBr₄ | (40) | " (0.4) | 90° C, 6 hr | Br,Br,Br product | (10) | Cl,Br,Br,Br product | (72) |

*Identified by the gas chromatographic retention time which was the same as that of an authentic sample obtained by introduction of dry hydrogen chloride into 1,1,1-trichloro-4-methyl-3-pentene.
**Identified by the gas chromatographic retention time which was the same as that of an authentic sample obtained by introduction of chlorine gas into 1,1,1-trichloro-4-methyl-3-pentene.

EXAMPLE 28

In 4,000 g of chloroform was dissolved 400 g of dimethyl vinyl carbinol and, following the addition of 30 g of tert-butyl perbenzoate, the solution was reacted at 110° C for 30 hours. After that time, the unreacted dimethyl vinyl carbinol and chloroform were removed by distillation under reduced pressure. As the residue was obtained 835 g of a reddish-yellow viscous fluid.

Gas-chromatographic analysis of this product revealed that the purity of 1,1,1-trichloro-4-methyl-4-pentanol was 90.4%, the amount of impurity 1,1,3-trichloro-4-methyl-4-pentanol being 8.7%.

The above residue was distilled in vacuo to obtain 732 g of high-purity 1,1,1-trichloro-4-methyl-4-pentanol as a fraction boiling at 60° - 61.5° C (0.3 mmHg). This product, on standing, provides white crystals.

The structural identification for 1,1,1-trichloro-4-methyl-4-pentanol was carried out in the same manner as Example 1. The above product was found to be identical with the 1,1,1-trichloro-4-methyl-4-pentanol obtained in Example 1.

Then, to 732 g of 1,1,1-trichloro-4-methyl-4-pentanol was added 7.3 g of p-toluenesulfonic acid and the mixture was heated at 155° - 160° C for 1.5 hours, the by-product water being azeotropically removed. The reaction mixture was as such distilled under a reduced pressure of 200 mmHg and the distillate was dried over sodium sulfate and fractionally distilled. By the above procedure was obtained 62 g of 1,1,1-trichloro-4-methyl-4-pentene as a fraction boiling at 73° - 74° C (20 mmHg), together with 536 g of 1,1,1-trichloro-4-methyl-3-pentene as a fraction boiling at 74° - 77° C (20 mmHg).

The structural identification for 1,1,1-trichloro-4-methyl-4-pentene and 1,1,1-trichloro-4-methyl-3-pentene was carried out by the same procedures as those described in Example 1. These compounds were in agreement with the 1,1,1-trichloro-4-methyl-4-pentene and 1,1,1-trichloro-4-methyl-3-pentene, respectively, of Example 1.

A three-necked flask of 500 ml capacity was filled with 186 g of the above 1,1,1-trichloro-4-methyl-3-pentene and, on a water bath, 183 g of 1,5-diazabicyclo[5,4,0]undecene-5(DBU) was added dropwise. After the dropwise addition was completed, the mixture was reacted at room temperature for 1 hour and, then, at 70° C for 2 hours. The reaction mixture thus obtained was poured in 500 ml of water and extracted with ether. The extract was rinsed with water, dehydrated and distilled under reduced pressure to remove the solvent. The residue was further distilled in vacuo to recover 137 g of 1,1-dichloro-4,4-dimethylbutandiene as a fraction boiling at 64° - 65° C (20 mmHg). The structure of this compound was identified by the following methods.

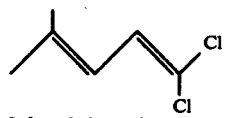

Infrared absorption spectrum:

$\begin{cases} 1645, 1580, 1448, 1380, 1270, 1052, 910, 850, \\ 818, 670 \text{ cm}^{-1} \end{cases}$ Mass spectrum:

$\begin{cases} 150/152/154 \\ (\text{Cl} \times 2) [\text{M}]^+ \end{cases}$

115/117 (Cl × 1)
[M]$^+$—Cl

Nuclear magnetic resonance spectrum: (in CCl$_4$, ppm)

$\begin{cases} 1.70, 1.77, \text{ each s, 6H, CH}_3\text{—, } 5.93 \text{ d, 1H, —CH=,} \\ 6.56 \text{ d, 1H, —CH=} \end{cases}$

EXAMPLE 29

A three-necked flask of 300 ml capacity was filled with 130.2 g of 1,1,1-trichloro-4-methyl-3-pentene as obtained by a procedure similar to that described in Example 1 and a solution of 23 g of sodium metal in 150 ml of methanol was added dropwise at 65° C. After the dropwise addition had been completed, the reaction was further continued at that temperature for 3 hours. After cooling, the resultant crystals were removed by filtration under reduced pressure. The filtrate was concentrated to 150 ml under reduced pressure, poured in water and extracted with ether. The extract was rinsed with a saturated aqueous solution of sodium chloride, dehydrated, and distilled under reduced pressure to remove the solvent. On vacuum distillation of the residue, there was obtained 98.7 g of 1,1-dichloro-4,4-dimethylbutadiene.

EXAMPLE 30

To 65 g of 1,1,1-trichloro-4-methyl-3-pentene was added 30 g of powdered potassium hydroxide and, under stirring, the reaction was carried out at 120° - 125° C for 5 hours. The reaction mixture was allowed to cool and, then, poured in water, followed by extraction with ether. The extract was rinsed with water and dehydrated. The solvent was then distilled off under reduced pressure and the residue was subjected to vacuum distillation. By the described procedure was obtained 46.7 g of 1,1-dichloro-4,4-dimethylbutadiene.

EXAMPLES 31 - 38

Examples 31 - 38

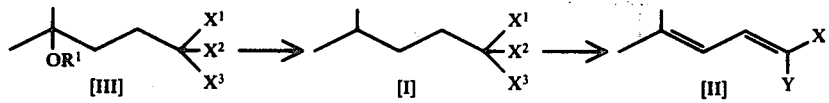

As in Example 28, each compound [III] was heated in the presence of an acid catalyst to remove R'OH and the resultant compound [I] was fractionated by distillation to isolate 1,1,1-trihalogeno-4-methyl-3-pentene. This last-mentioned compound was reacted with a basic reagent to obtain the corresponding 1,1-diahalogeno-4,4-dimethylbutadiene. The results are set forth in Table 4. The compounds [III] employed were each synthesized by reacting the corresponding

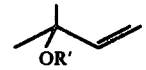

in 10 times its weight of chloroform and in the presence of a radical initiator at a temperature in the range of 100° to 130° C.

Table 4

| Ex. | Compound [III] (mole) | Acid catalyst (mole %)* | Conditions of removal of R'OH | [III] → [I] % Conversion of compound [III] % Selectivity for compound [I] | Ratio of $\overset{X^1}{\underset{X^3}{\diagdown}}\!\!\!\!\diagup\!\!\!\!X^2$ : $\overset{X^1}{\underset{X^3}{\diagdown}}\!\!\!\!\diagup\!\!\!\!X^2$ |
|---|---|---|---|---|---|
| 31 | (structure with OH, Cl, Cl, Cl) (1 mole) | Lauryl sulfonate (1.0) | 155° C, 2 hrs. | 98.8 / 99.0 | 15 : 85 |
| 32 | " | $H_2SO_4$ (0.5) | 130° C, 4 hrs. | 98.4 / 96.5 | 20 : 80 |
| 33 | " | $V_2O_5$ (1.5) | 140° C, 3 hrs. | 93.1 / 97.7 | 25 : 75 |
| 34 | (structure with $OC_2H_5$, Cl, Cl, Cl) (0.5 mole) | p-Toluenesulfonic acid (0.7) | 160° C, 1.5 hr. | 97.2 / 97.9 | 15 : 85 |
| 35 | (structure with $OCCH_3$ (=O), Cl, Cl, Cl) (0.5 mole) | " | " | 92.4 / 96.0 | " |
| 36 | (structure with OH, Br, Br, Br) (0.5 mole) | $H_2SO_4$ | 130° C, 3 hrs. | 96.7 / 95.4 | 22 : 78 |
| 37 | " | $V_2O_5$ (1.5) | 140° C, 3 hrs. | 97.3 / 95.7 | 27 : 73 |
| 38 | (structure with $OC_2H_5$, Br, Br, Br) (0.5 mole) | p-Toluenesulfonic acid (0.7) | 150° C, 2 hrs. | 96.8 / 93.4 | 17 : 83 |

| Ex | Compound [I] (mole) | Base (mole) | [I] → [II] Conditions of removal of hydrogen halide | Compound [II], % yield** |
|---|---|---|---|---|
| 31 | (structure with Cl, Cl, Cl) (0.2) | DBN | Room temp., 1.5 hrs. 65° C, 2.5 hrs. | 93.2 |
| 32 | " | $NaNH_2$ | 70° C, 4 hrs. | 88.9 |
| 33 | " | $Ca(OH)_2$ | 110° C, 4 hrs. | 90.2 |
| 34 | " | DBU | Room temp., 1.5 hrs. 65° C, 2.0 hrs. | 94.6 |
| 35 | " | NaOMe | 65° C, 5 hrs. | 91.2 |
| 36 | (structure with Br, Br, Br) (0.2) | NaOEt | 70° C, 5 hrs. | 92.0 |
| 37 | " | NaOBu$^t$ | " | 87.1 |
| 38 | " | KOBu$^t$ | 60° C, 3 hrs. | 93.4 |

[Notes]
*Mole % of catalyst based on compound [III]
**Yield from compound [I]

We claim as our invention:
1. A 1,1,1-trihalogeno-4-methylpentene of the formula

$$Z-CH_2C\underset{X^3}{\overset{X^1}{\diagdown}}\!\!\!\!\diagup\!\!\!\!X^2$$

wherein $X^1$, $X^2$ and $X^3$ are the same or different and each represents a halogen atom and Z is a group of the formula

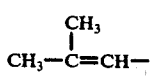

or a group of the formula

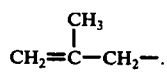

2. A 1,1,1-trihalogeno-4-methylpentene as set forth in claim 1, which has the formula:

$$CH_3-\underset{\underset{CH_3}{|}}{C}=CH-CH_2-CCl_3.$$

3. A 1,1,1-trihalogeno-4-methylpentene as set forth in claim 1, which has the formula:

$$CH_2=\underset{\underset{CH_3}{|}}{C}-CH_2-CH_2-CCl_3.$$

4. A process for producing a 1,1,1-trihalogeno-4-methylpentene of the formula $$Z-CH_2C\underset{\diagdown X^3}{\overset{\diagup X^1}{-X^2}} \qquad I$$

wherein Z is a group of the formula $$CH_3-\underset{\underset{CH_3}{|}}{C}=CH-$$

or a group of the formula $$CH_2=\underset{\underset{CH_3}{|}}{C}-CH_2-$$

and $X^1$, $X^2$ and $X^3$ are the same or different and each represents a halogen atom, which comprises removing $R^1OH$ from a compound of the formula $$CH_3-\underset{\underset{OR^1}{|}}{\overset{\overset{CH_3}{|}}{C}}-CH_2CH_2C\underset{\diagdown X^3}{\overset{\diagup X^1}{-X^2}} \qquad III$$

wherein $R^1$ is a hydrogen atom or an alkyl, cycloalkyl, aryl, aralkyl or acyl group; and $X^1$, $X^2$ and $X^3$ are as defined above in the presence of an effective amount of an acid catalyst or of an effective amount of at least one member selected from the group consisting silica gel, aluminum silicate, kieselguhr, pumice, Fuller's earth, activated alumina and activated carbon.

5. A process as set forth in claim 4 wherein the reaction is carried out at a temperature of from room temperature to about 160° C in the presence of 0.01 to 30%, based on the weight of said compound of formula III, of an acid catalyst.

6. A process as set forth in claim 5 wherein the temperature is from room temperature to 120° C.

7. A process as set forth in claim 5 wherein said acid catalyst is present in an amount within the range of 0.1 to 10%.

8. A process as set forth in claim 5 wherein the reaction is carried out at a temperature of from 80° to 250° C in gaseous or liquid phase in the presence of at least one member selected from the group consisting of silica gel, aluminum silicate, kieselguhr, pumice, Fuller's earth, activated alumina and activated carbon.

9. A process for producing a 1,1,1-trihalogeno-4-methyl-3-pentene, which comprises removing $R^1OH$ from a compound of the formula $$CH_3-\underset{\underset{OR^1}{|}}{\overset{\overset{CH_3}{|}}{C}}-CH_2CH_2C\underset{\diagdown X^3}{\overset{\diagup X^1}{-X^2}} \qquad III$$

wherein $R^1$ is a hydrogen atom or an alkyl, cycloalkyl, aryl, aralkyl or acyl group and $X^1$, $X^2$ and $X^3$ are the same or different and each represents a halogen atom in the presence of an effective amount of an acid catalyst or of an effective amount of at least one member selected from the group consisting of silica gel, aluminum silicate, kieselguhr, pumice, Fuller's earth, activated alumina and activated carbon to obtain a mixture of a 1,1,1-trihalogeno-4-methyl-4-pentene of the formula $$CH_2=\underset{\underset{CH_3}{|}}{C}-CH_2CH_2C\underset{\diagdown X^3}{\overset{\diagup X^1}{-X^2}} \qquad I''$$

wherein $X^1$, $X^2$ and $X^3$ are as defined above and a 1,1,1-trihalogeno-4methyl-3-pentene of the formula $$CH_3-\underset{\underset{CH_3}{|}}{C}=CHCH_2C\underset{\diagdown X^3}{\overset{\diagup X^1}{-X^2}} \qquad I'$$

wherein $X^1$, $X^2$ and $X^3$ are as defined above and subjecting said mixture to fractional distillation to isolate said 1,1,1-trihalogeno-4-methyl-3-pentene with a first-emerging fraction rich in said 1,1,1-trihalogeno-4-methyl-4-pentene being recycled to the reaction system.

10. A process as set forth in claim 9 wherein the reaction is carried out at a temperature of from room temperature to about 160° C in the presence of 0.01 to 30%, based on the weight of said compound of formula III, of an acid catalyst.

11. A process as set forth in claim 10 wherein the temperature is from room temperature to 120° C.

12. A process as set forth in claim 10 wherein said acid catalyst is present in an amount within the range of 0.1 to 10%.

13. A process as set forth in claim 9 wherein the reaction is carried out at a temperature of from 80° to 250° C in gaseous or liquid phase in the presence of at least one member selected from the group consisting of silica gel, aluminum silicate, kieselguhr, pumice, Fuller's earth, activated alumina and activated carbon.

14. A process for producing a 1,1,1-trihalogeno-4-methylpentene of the formula $$Z-CH_2C\underset{\diagdown X^3}{\overset{\diagup X^1}{-X^2}} \qquad I$$

wherein $X^1$, $X^2$ and $X^3$ are the same or different and each represents a halogen atom and Z is a group of the formula

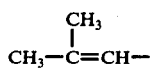

or a group of the formula

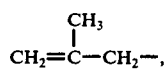

which comprises adding a haloform to a dimethyl vinyl carbinol compound of the formula

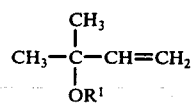 IV wherein $R^1$ is a hydrogen atom or an alkyl, cycloalkyl, aryl, aralkyl or acyl group under radical-reaction conditions to obtain a compound of the formula

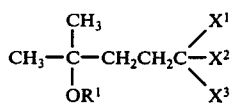 III wherein $R^1$, $X^1$, $X^2$ and $X^3$ are as defined above and removing $R^1OH$ from the last-mentioned compound III in the presence of an effective amount of an acid catalyst or of an effective amount of at least one member selected from the group consisting of silica gel, aluminum silicate, kieselguhr, pumice, Fuller's earth, activated alumina and activated carbon.

15. A process as set forth in claim 14 wherein the reaction is carried out at a temperature of from room temperature to about 160° C in the presence of 0.01 to 30%, based on the weight of said compound of formula III, of an acid catalyst.

16. A process as set forth in claim 15 wherein the temperature is from room temperature to 120° C.

17. A process as set forth in claim 15 wherein said acid catalyst is present in an amount within the range of 0.1 to 10%.

18. A process as set forth in claim 14 wherein the reaction is carried out at a temperature of from 80° to 250° C in gaseous or liquid phase in the presence of at least one member selected from the group consisting of silica gel, aluminum silicate, kieselguhr, pumice, Fuller's earth, activated alumina and activated carbon.

19. A process as set forth in claim 14 wherein $R^1$ in formula IV is a hydrogen atom.

20. A process as set forth in claim 14 wherein said haloform is chloroform or bromoform.

21. A process as set forth in claim 14 wherein the reaction under said radical-reaction conditions is conducted in the presence of a radical-reaction initiator and at a temperature in the range of 70° to 180° C.

22. A process as set forth in claim 14 wherein the reaction under said radical-reaction conditions is conducted under irradiation and at a temperature in the range of room temperature to 100° C.

23. A process for producing a 1,1,1-trihalogeno-4-methyl-3-pentene of the formula

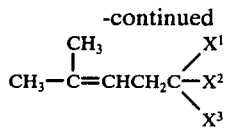 I''' wherein $X^1$, $X^2$ and $X^3$ are the same or different and each represents a halogen atom, which comprises isomerizing a 1,1,1-trihalogeno-4-methyl-4-pentene of the formula

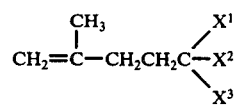 I'' wherein $X^1$, $X^2$ and $X^3$ are as defined above by heating at a temperature of from 80° to 200° C in the presence of 0.001 to 30%, based on the weight of said 1,1,1-trihalogeno-4-methyl-4-pentene, of at least one member selected from the group consisting of a transition metal of Group 6B, Group 7B or Group 8 of the Periodic Table of the Elements, a compound of said transition metal and an acid catalyst.

24. A process as set forth in claim 23 wherein said temperature is in the range of 110° to 170° C.

25. A processas set forth in claim 23 wherein the proportion of any of said transition metals and compounds of transition metals or of said acid catalyst is in the range of 0.1 to 10 weight percent.

26. A process for producing a 1,1-dihalogeno-4-methyl-1,3-pentadiene of the formula

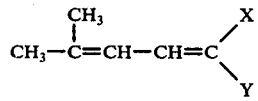 II wherein X and Y are the same or different and each represents a halogen atom, which comprises treating a 1,1,1-trihalogeno-4- methyl-3-pentene of the formula

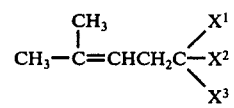 I' wherein $X^1$, $X^2$ and $X^3$ are the same or different and each represents a halogen atom with a basic reagent at a temperature of from room temperature to 150° C.

27. A process as set forth in claim 26 wherein said basic reagent is at least one member selected from the group consisting of an alkali or alkaline earth metal hydroxide, a metal alcoholate, an alkali metal hydride, an alkali metal amide, an amine and an organolithium compound.

28. a process as set forth in claim 27 wherein said basic reagent is an alkali metal alcoholate, alkali metal hydride or alkali metal hydroxide.

29. A process as set forth in claim 26 wherein said temperature is from 50 to 130° C.

30. A process for producing a 1,1-dihalogeno-4- methyl-1,3-pentadiene of the formula -continued

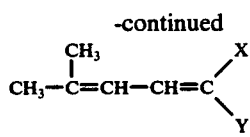

wherein X and Y are the same or different and each represents a halogen atom, which comprises adding a haloform to a dimethyl vinyl carbinol compound of the formula

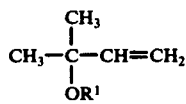
IV wherein $R^1$ is a hydrogen atom or an alkyl, cycloalkyl, aryl, aralkyl or acyl group under radical-reaction conditions to obtain a compound of the formula

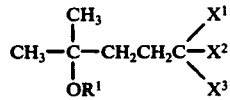
III wherein $R^1$ is as defined above and $X^1$, $X^2$ and $X^3$ are the same or different and each represents a halogen atom; removing $R^1OH$ from the compound III in the presence of an effective amount of an acid catalyst or an effective amount of at least one member selected from the group consisting of silica gel, aluminum silicate, kieselguhr, pumice, Fuller's earth, activated alumina and activated carbon to obtain a mixture of a 1,1,1-trihalogeno-4-methyl-4-pentene of the formula

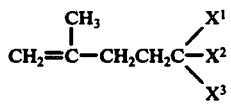
I"

wherein $X^1$, $X^2$ and $X^3$ are as defined above and a 1,1,1-trihalogeno- 4-methyl-3-pentene of the formula

I'

-continued

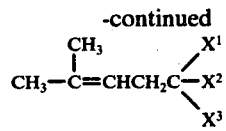

wherein $X^1$, $X^2$ and $X^3$ are as defined above; subjecting said mixture to fractional distillation to isolate said 1,1,1-trihalogeno-4-methyl-3-pentene and treating said 1,1,1-trihalogeno- 4-methyl-3-pentene with a basic reagent at a temperature of from room temperature to 150° C.

31. A process as set forth in claim 30 wherein $R^1$ in formula IV is a hydrogen atom.

32. A process as set forth in claim 30 wherein said haloform is chloroform or bromoform.

33. A process as set forth in claim 30 wherein the reaction under said radical-reaction conditions is conducted in the presence of a radical-reaction intitiator and at a temperature in the range of 70° to 180° C.

34. A process as set forth in claim 30 wherein the reaction under said radical-reaction conditions is conducted under irradiation and at a temperature in the range of room temperature to 100° C.

35. A process as set forth in claim 30 wherein the removal of $R^1OH$ is carried out at a temperature of from room temperature to about 160° C in the presence of 0.01 to 30%, based on the weight of said compound of formula III, of an acid catalyst.

36. A process as set forth in claim 35 wherein the temperature is from room temperature to 120° C.

37. A process as set forth in claim 35 wherein said acid catalyst is present in an amount within the range of 0.1 to 10%.

38. A process as set forth in claim 30 wherein the removing of $R^1OH$ is carried out at a temperature of from 80° C to 250° C in gaseous or liquid phase in the presence of at least one member selected from the group consisting of silica gel, aluminum silicate, kieselguhr, pumice, Fuller's earth, activated alumina and activated carbon.

39. A process as set forth in claim 30 wherein the basic reagent is at least one member selected from the group consisting of an alkali or alkaline earth metal hydroxide, a metal alcoholate, an alkali metal hydride, an alkali metal amide, an amine and an organolithium compound.

40. A process as set forth in claim 39 wherein said basic reagent is an alkali metal alcoholate, alkali metal hydride or alkali metal hydroxide.

41. A process as set forth in claim 30 wherein the treatment with a basic reagent is carried out at a temperature of from 50° to 130° C.

* * * * *